(12) United States Patent
Haas

(10) Patent No.: US 7,585,328 B2
(45) Date of Patent: Sep. 8, 2009

(54) MINIMALLY INVASIVE KNEE ARTHROPLASTY

(76) Inventor: Steven B. Haas, 535 E. 70$^{th}$ St., New York, NY (US) 10021

( * ) Notice: Subject to any disclaimer, the term of this patent is extended or adjusted under 35 U.S.C. 154(b) by 627 days.

(21) Appl. No.: 10/984,208

(22) Filed: Nov. 8, 2004

(65) Prior Publication Data
US 2007/0051378 A1 Mar. 8, 2007

Related U.S. Application Data

(60) Provisional application No. 60/518,018, filed on Nov. 6, 2003.

(51) Int. Cl.
*A61F 2/38* (2006.01)
(52) U.S. Cl. .................................. 623/20.14
(58) Field of Classification Search ............... 623/20.11, 623/20.14
See application file for complete search history.

(56) References Cited

U.S. PATENT DOCUMENTS

| 5,122,144 | A | 6/1992 | Bert et al. |
| 5,860,980 | A | 1/1999 | Axelson, Jr. et al. |
| 6,342,075 | B1 | 1/2002 | MacArthur |
| 6,984,248 | B2 * | 1/2006 | Hyde, Jr. ................. 623/18.12 |
| 7,371,240 | B2 * | 5/2008 | Pinczewski et al. ........... 606/88 |
| 2003/0130665 | A1 * | 7/2003 | Pinczewski et al. ........... 606/88 |
| 2003/0153978 | A1 * | 8/2003 | Whiteside ................ 623/20.21 |
| 2004/0153066 | A1 * | 8/2004 | Coon et al. ................... 606/54 |
| 2006/0167460 | A1 * | 7/2006 | Pinczewski et al. ........... 606/88 |
| 2007/0239167 | A1 * | 10/2007 | Pinczewski et al. ........... 606/87 |

OTHER PUBLICATIONS

Orthopedics: Advancements in Minimally Invasive Total Knee Arthroplasty, Alfred J. Tria, Jr., MD, Orthopedics® Aug. 2003 Supplement, pp. 1-10 http://www.orthobluejournal.com/supp/0803/tria.asp (Oct. 12, 2004).
Microplasty™ Minimally Invasive Knee Technique, Information for Health Care Professionals http://www.biomet.com/surgeons/products/microplasty/knee_ technique, 20 pages (Oct. 13, 2004).
NexGen® Complete Knee Solution MIS Quad-Sparing™ Instrumentation Zimmer. 02 pages (Apr. 2, 2008) http//:www.zimmer.com/ctl?prcat=M3&prod=y&template=MP&action=1&op=global&id=9403&pr=Y.

* cited by examiner

*Primary Examiner*—Thomas J Sweet
(74) *Attorney, Agent, or Firm*—Kilpatrick Stockton LLP

(57) ABSTRACT

A anteromedial approach to arthroplasty on a knee joint of a patient. The method of arthroplasty includes an arthrotomy that includes dissecting from medial to the tibial tubercle and around the medial border of the patella and up to the proximal border of the patella.

18 Claims, 4 Drawing Sheets

300 Exposure

302 Extend leg to retract patella laterally

304 Excise fat pad leaving a small amount of fat deep under the patella tendon

306 Divide the anterior horn of the medial meniscus

308 Dissect around the proximal medial tibia

310 Place a retractor on the proximal medial tibia

312 Release soft tissue attachments extending around the proximal medial tibia

314 Make a small window along the anterior surface of the distal femur

FIG. 3

MINIMALLY INVASIVE KNEE ARTHROPLASTY

RELATED APPLICATION DATA

This application claims the benefit of U.S. Ser. No. 60/518,018 filed Nov. 6, 2003 entitled "Minimally Invasive Knee Arthroplasty Surgical Technique and Related Instrumentation," incorporated herein by this reference.

FIELD OF INVENTION

The invention relates to a method of arthroplasty on a knee joint of a patient. More particularly, it relates to minimally invasive surgical techniques used to perform arthroplasty on a knee joint of a patient.

BACKGROUND

Arthritis of the knees can wear away and destroy the surfaces of the knee joint and ultimately lead to conditions that require a knee replacement. In osteoarthritis, which is usually caused by old age, angular deformity, or old fractures, the surfaces of the knee gradually wear out. Likewise systemic arthritis affects the synovium or membrane tissue in the joint destroying the surface of the joint. In both osteoarthritis and systemic arthritis, when the surface of the joint is worn away, walking and other activities become difficult and painful. In many cases, knee replacements are performed to address these issues.

Knee replacement surgery or arthroplasty typically involves a resurfacing of the knee joint in which the femur, or thigh bone, and/or tibia, or shinbone, are covered with artificial materials such as metal or plastic thereby replacing the irregular surfaces caused by the arthritis with smooth surfaces. The undersurface of the patella, or knee cap, may also be replaced with artificial materials. Historically, the actual knee replacement procedure involved either general or epidural anesthesia with a four to six day hospitalization with the surgery itself taking about two hours.

There are three general types of knee replacements: total knee replacements (TKR), partial knee replacement (also called a unicompartmental knee replacement), and knee revision. A TKR resurfaces the knee joint by removing the diseased bone and cartilage. The end of the long bones of the knee joint, the femur and the tibia, are removed and replaced with artificial materials. The portion of the femur that is removed is usually replaced with metal (e.g. titanium or zirconium), while the portion of the tibia that is removed is usually replaced with plastic. The replacement components may be either cemented in place or inserted in a cementless manner.

A partial knee replacement involves installing an implant on one side of the knee, rather than over the entire surface of the knee joint. A unicondylar knee replacement is done if part of the knee joint is damaged by arthritis and the other compartments have healthy, normal cartilage at surgery.

A knee revision involves fixing problems with an existing knee replacement. Knee replacements fail over time and require revision. This revision procedure may be more complex than a total knee replacement for a number of reasons including because removing the existing implant may weaken the bone and damage the surrounding ligaments supporting the knee. Because of these problems a special implant may be used or a bone graft may be required to reconstruct deficient areas.

Traditional instrumentation and surgical techniques used in open arthroplasty surgery are not easily adapted for use in minimally invasive knee surgery. Specifically, using traditional instrumentation with smaller incisions can lead to stretching of the skin and misalignment of the knee replacement components due to lack of visibility. Using nontraditional surgical techniques, on the other hand, provides the disadvantage of requiring the surgeon to re-learn the surgery and can lead to longer operative times, higher complication rates, and higher surgical costs.

SUMMARY

Methods of the present invention provide an anteromedial approach to knee arthroplasty to minimize the learning curve for surgeons while minimizing operation recovery time, blood loss, soft tissue damage, and incision length. The methods generally result in a faster, less painful return to function for the patient with a relatively small scar. One embodiment of the method of the present invention involves an arthrotomy made over the anterior aspects of the knee along the medial border of the patella. The position of this incision allows the knee arthroplasty to be performed without cutting the quad tendon and without everting, or turning outward, the patella.

In some embodiments of the present invention the knee arthroplasty is performed using a minimally invasive surgical technique and may be performed through an incision smaller than 10 inches, and preferably smaller than 5 inches.

BRIEF DESCRIPTION OF THE DRAWINGS

FIG. 3 illustrates the steps for performing an exposure during an arthroplasty in accordance with one embodiment of the present invention.

DETAILED DESCRIPTION

Surgical methods of the present invention include an anteromedial approach to arthroplasty on a knee joint of a patient. These methods of arthroplasty include an arthrotomy, or surgical incision into the knee joint, made over the anterior aspects of the knee along the medial border of the patella. In one embodiment, the arthrotomy includes a dissection from medial to the tibial tubercle and around the medial border of the patella and up to the proximal border of the patella. The arthrotomy may further include identifying the distal extend of the vastus medialis, determining the orientation of the fibers, making an oblique cut into the vastus medialis, and separating the muscle fibers.

In one embodiment of the present method, the arthrotomy is followed by an exposure step. Different embodiments of the present invention involve combinations of one or more of: retracting the patella laterally to expose the knee, excising the fat pad both medially and laterally and leaving a small amount of fat deep under the patella tendon, dividing the anterior horn of the medial meniscus, dissecting around the proximal medial tibia, placing a retractor on the proximal medial tibia, releasing the proximal soft tissue attachments extending around the proximal media tibia, and making a small window along the anterior surface of the distal femur.

In one embodiment of the present invention, prior to an arthrotomy step, there is a step of making a longitudinal incision over the anterior aspect of the knee along the medial border of the patella extending approximately from the proximal tibia tubercle to the proximal extent of the patella to approximately the patella.

In one embodiment of the invention, prior to making the incision over the anterior aspect of the knee along the medial border of the patella, there is a first step of positioning the leg on the operating table so that the knee is flexed 70° to 90°.

Figure 1:
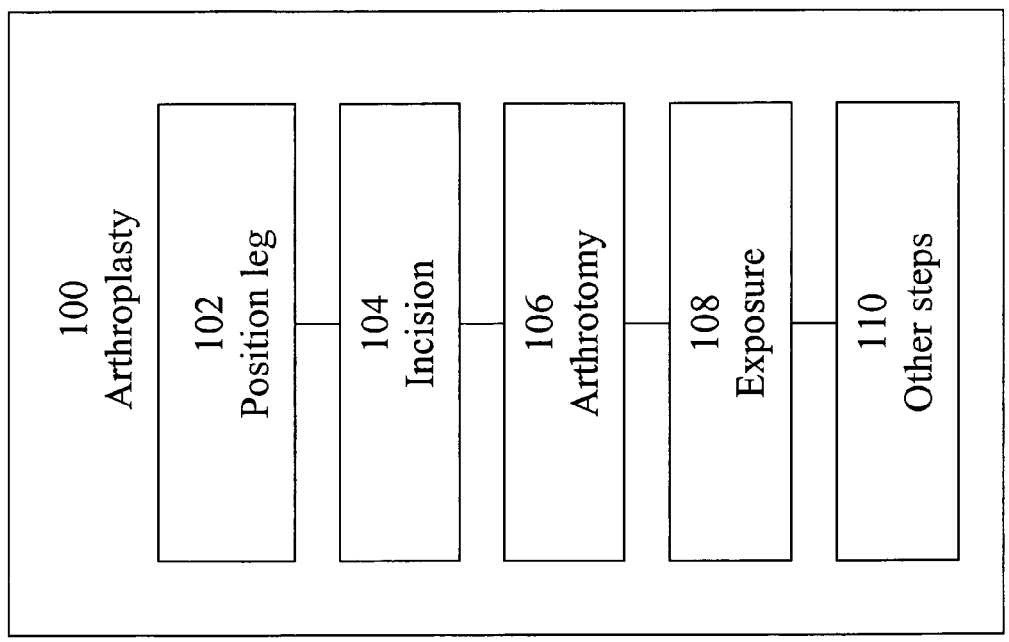
FIG. 1 illustrates the steps for performing an arthroplasty in accordance with one embodiment of the present invention.

Referring to FIG. 1, one embodiment of a method of arthroplasty on a knee joint of a patient in accordance with the present invention includes positioning the patients leg 102, making one or more incisions 104, performing an anteromedial arthrotomy 106, an exposure 108, among other steps 110. The following paragraphs provides examples of each of these steps.

1. Leg Position

During the procedure the knee is flexed to 70° to 90°. Hyperextension is used only intermittently for specific parts of the procedure, such as insertion of a tibial component. In order to aid in holding the leg, a sandbag may be placed across from the contra-lateral ankle when positioning the patient on the operating table.

2. Incision

With the leg fully extended, a longitudinal incision is made over the anterior aspects of the knee along the medial border of the patella. The incision extends approximately from the proximal tibial tubercle to the proximal extent of the patella to one finger's breadth proximal to the patella.

3. Arthrotomy 200

Figure 2:
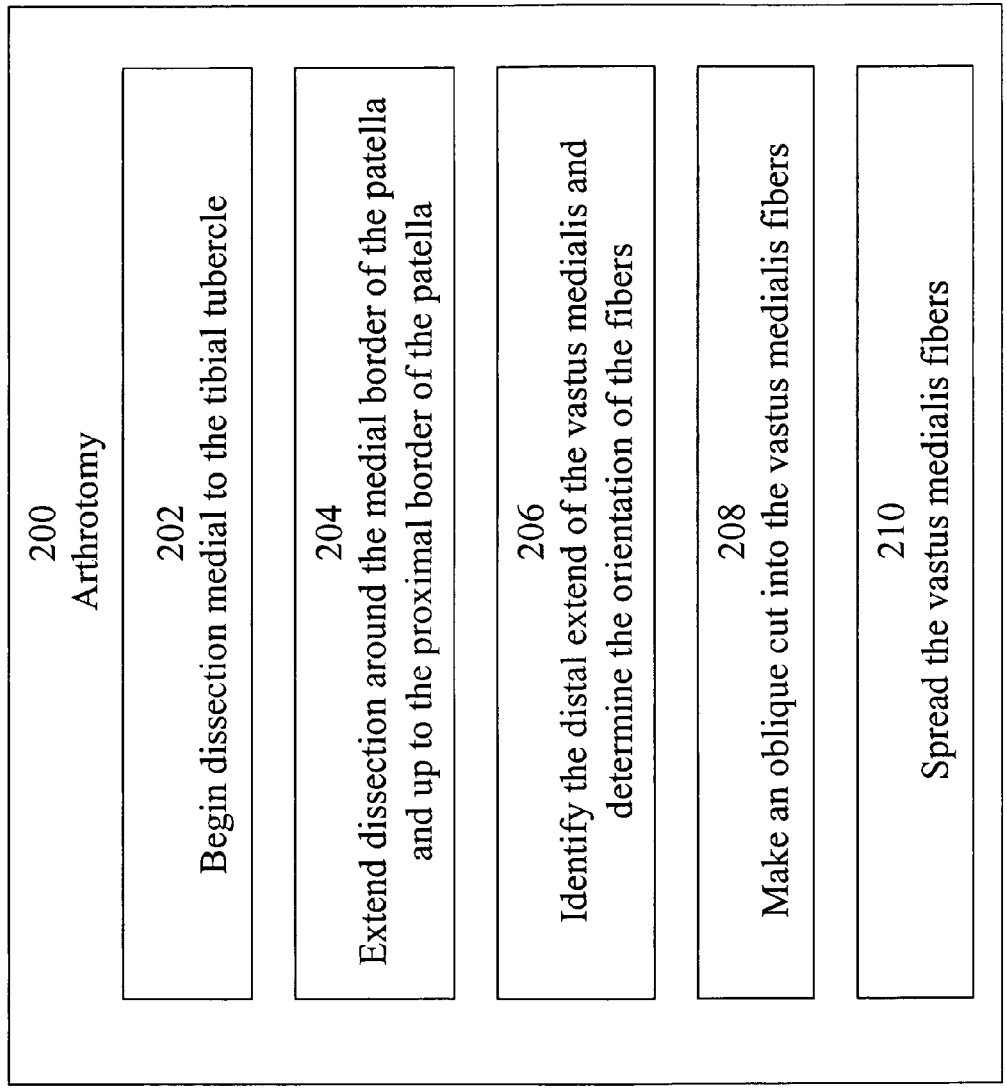
FIG. 2 illustrates the steps for performing an arthrotomy in accordance with one embodiment of the present invention.
Figure 4:
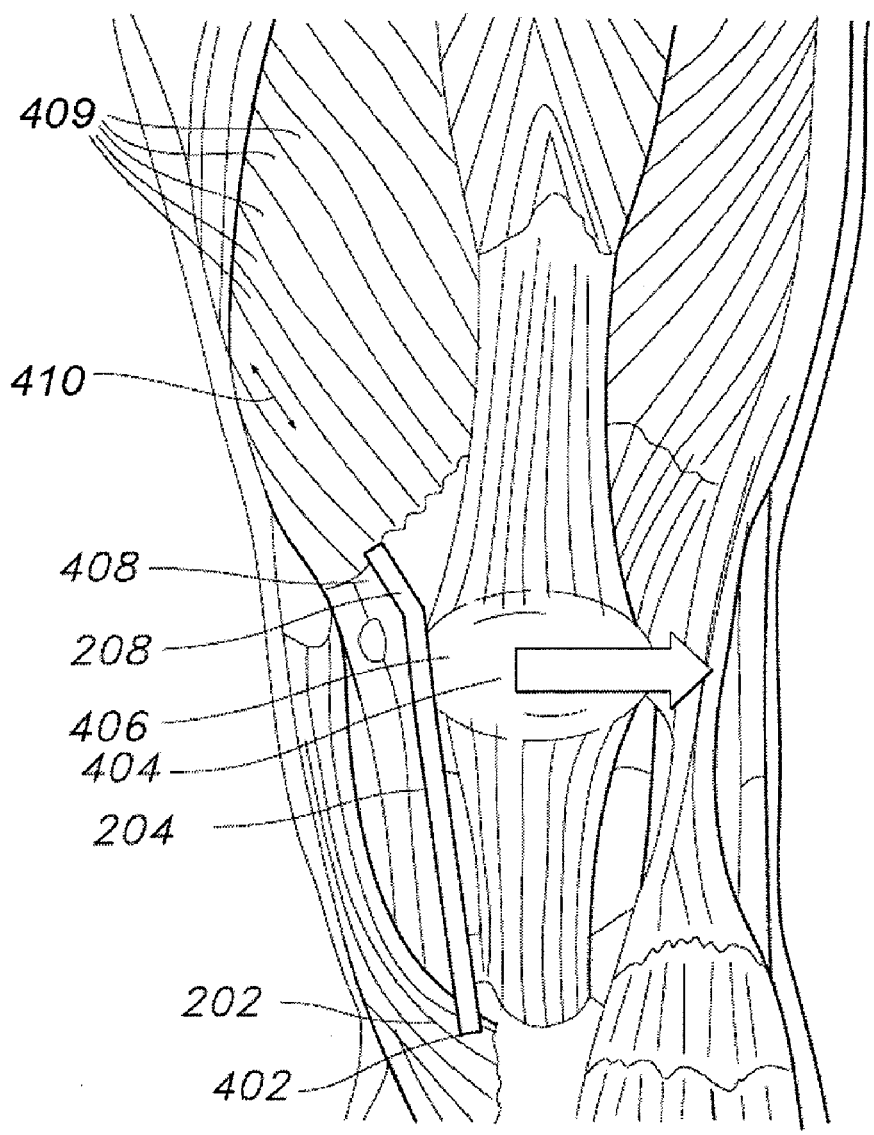
FIG. 4 illustrates an exemplary surgical method with respect to the anatomy of a knee in accordance with one embodiment of the present invention.

As recited and shown in FIGS. 2 and 4, respectively, begin the dissection 401 medial to the tibial tubercle 402, as recited in block 202. Extend the dissection 401 around the medial border 406 of the patella 404, as recited in block 204. The arthrotomy extends up to the proximal border of the patella 404, as is also recited in block 204.

The distal extend of the vastus medialis 408 is identified and the orientation 410 of the fibers 409 is determined, as recited in block 206. An oblique cut is made into the vastus medialis 408, as shown in block 208 and the muscle fibers 409 are then spread, as recited in block, 210, approximately 2 centimeters.

4. Exposure

As shown in FIG. 3, with the leg extended, the patella is retracted laterally 302. The fat pad is excised both medially and laterally leaving a small amount of fat deep under the patella tendon 304. The anterior horn of the medial meniscus is divided 306 and dissection is carried around the proximal medial tibia 308 using electrocautery and boxed osteotome or other surgical knife. A retractor is placed on the proximal medial tibia 310. The proximal soft tissue attachments extending around the proximal medial tibia are released 312 in a standard fashion.

A small window is made along the anterior surface of the distal femur 314 with the use of electrocautery to reference the anterior cortex.

5. Other Steps

Other steps as required are carried out to complete the knee arthroplasty.

Modifications, adaptations, changes, deletions, and additions may be made to various embodiments of the present invention as disclosed in this document without departing from the scope or spirit of the invention.

What is claimed is:

1. A method of arthroplasty on a knee joint of a patient comprising an arthrotomy comprising dissecting beginning at a position medial to a tibial tubercle, extending to a medial border of a patella, up to a proximal border of the patella, and obliquely into the vastus medialis in a direction of fibers of the vastus medialis.

2. The method of claim 1 wherein the method further comprises identifying the distal extend of the vastus medialis and the direction of the fibers of the vastus medialis prior to dissecting obliquely into the vastus medialis in the direction of the fibers.

3. The method of claim 2 wherein the method further comprises separating the muscle fibers.

4. The method of claim 3 further comprising retracting the patella laterally to expose the knee.

5. The method of claim 3 further comprising retracting the patella laterally without everting the patella to expose the knee.

6. The method of claim 4 further comprising excising the fat pad both medially and laterally and leaving a small amount of fat deep under the patella tendon.

7. The method of claim 6 further comprising dividing the anterior horn of the medial meniscus and dissecting around the proximal medial tibia.

8. The method of claim 7 further comprising placing a retractor on the proximal soft tissue attachments extending around the proximal medial tibia.

9. The method of claim 8 further comprising making a small window along the anterior surface of the distal femur.

10. The method of claim 9 further comprising, prior to the arthrotomy, making a longitudinal incision over an anterior aspect of the knee along the medial border of the patella extending approximately from the tibial tubercle to the border of the patella to approximately the patella.

11. The method of claim 10 further comprising, during preparation of the bones, positioning a leg of the patient on an operating table so that the knee is flexed 70° to 90°.

12. The method of claim 10 further comprising, prior to making the longitudinal incision in the knee, positioning a leg of the patient on an operating table so that the knee is flexed 70° to 90°.

13. A method of arthroplasty on a knee joint of a patient comprising:

an arthrotomy step comprising dissecting beginning at a position medial to a tibial tubercle and extending to a medial border of a patella and up to a proximal border of the patella, identifying the distal extend of the vastus medialis and determining the orientation of the fibers, extending the dissection with an oblique cut into the vastus medialis in a direction of the fibers and separating the muscle fibers; and an exposure step comprising retracting the patella laterally to expose the knee, excising the fat pad both medially and laterally and leaving a small amount of fat deep under the patella tendon, dividing the anterior horn of the medial meniscus and dissecting around the proximal medial tibia, placing a retractor on the proximal soft tissue attachments extending around the proximal medial tibia, and making a small window along the anterior surface of the distal femur.

14. The method of claim 13 further comprising, prior to the arthrotomy, making a longitudinal incision over an anterior aspect of the knee along the medial border of the patella extending approximately from the tibial tubercle to the border of the patella to approximately the patella.

15. The method of claim 14 further comprising, during preparation of the bones, positioning a leg of the patient on an operating table so that the knee is flexed 70° to 90°.

16. The method of claim 14 further comprising, prior to making the longitudinal incision in the knee, positioning a leg of the patient on an operating table so that the knee is flexed 70° to 90°.

17. A method of arthroplasty on a knee joint of a patient comprising:

identifying the distal extend of the vastus medialis and determining the orientation of the fibers;

dissecting from medial to a tibial tubercle and extending to a medial border of a patella, up to a proximal border of the patella, and obliquely into the vastus medialis in a direction of the muscle fibers; and separating the muscle fibers.

18. The method of claim 17 further comprising:

retracting the patella laterally to expose the knee;

excising the fat pad both medially and laterally and leaving a small amount of fat deep under the patella tendon;

dividing the anterior horn of the medial meniscus and dissecting around the proximal medial tibia;

placing a retractor on the proximal soft tissue attachments extending around the proximal medial tibia; and making a small window along the anterior surface of the distal femur.

* * * * *

UNITED STATES PATENT AND TRADEMARK OFFICE
CERTIFICATE OF CORRECTION

PATENT NO. : 7,585,328 B2
APPLICATION NO. : 10/984208
DATED : September 8, 2009
INVENTOR(S) : Steven B. Haas It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1178 days.

Signed and Sealed this

Fourteenth Day of December, 2010

David J. Kappos
*Director of the United States Patent and Trademark Office*